United States Patent [19]

Takai et al.

[11] Patent Number: 5,096,560

[45] Date of Patent: Mar. 17, 1992

[54] ELECTRODE FOR ELECTROCHEMICAL DETECTORS

[75] Inventors: Nobuharu Takai, Meguro; Yoshiteru Kageyama, Yokkaichi; Yoshiaki Sawada, Yokkaichi; Akira Yoshida, Yokkaichi, all of Japan

[73] Assignee: Mitsubishi Petrochemical Company Limited, Tokyo, Japan

[21] Appl. No.: 529,543

[22] Filed: May 29, 1990

[30] Foreign Application Priority Data

May 30, 1989 [JP] Japan .................... 1-136371
Mar. 22, 1990 [JP] Japan .................... 2-72666

[51] Int. Cl.$^5$ .................................. C25B 11/12
[52] U.S. Cl. .................................. 204/294; 204/400
[58] Field of Search .................. 204/294, 400; 73/61.1 C; 264/29.5

[56] References Cited

U.S. PATENT DOCUMENTS

| | | | |
|---|---|---|---|
| 3,477,940 | 11/1969 | Grangaard | 204/294 X |
| 4,294,893 | 10/1981 | Iemmi et al. | 204/294 X |
| 4,343,767 | 8/1982 | Long et al. | 422/70 |
| 4,369,104 | 1/1983 | Beckley | 204/286 |
| 4,470,892 | 9/1984 | Dasgupta et al. | 204/294 |
| 4,500,395 | 2/1985 | Nakamura | 204/294 |
| 4,506,028 | 3/1985 | Fukuda et al. | 502/101 |
| 4,576,706 | 3/1986 | Takata et al. | 204/409 |
| 4,804,455 | 2/1989 | Matson | 204/411 |
| 4,814,307 | 3/1989 | Funabashi et al. | 502/101 |

FOREIGN PATENT DOCUMENTS 1483100 4/1967 France .
41296 4/1979 Japan .

*Primary Examiner*—John Niebling
*Assistant Examiner*—Bruce F. Bell
*Attorney, Agent, or Firm*—Wegner, Cantor, Mueller & Player

[57] ABSTRACT

An electrode for a coulometric type of electrochemical detector, comprising a formed product of a porous, graphitic carbon having the following physical properties (1), (2) and (3):

(1) an average pore diameter of 0.1 to 50 μm,
(2) a specific surface area of 10 m$^2$/g or more, and
(3) an average interlaminar spacing ($d_{002}$) of carbon of 3.35 to 3.42 Å, as determined by X-ray diffraction analysis.

9 Claims, 3 Drawing Sheets

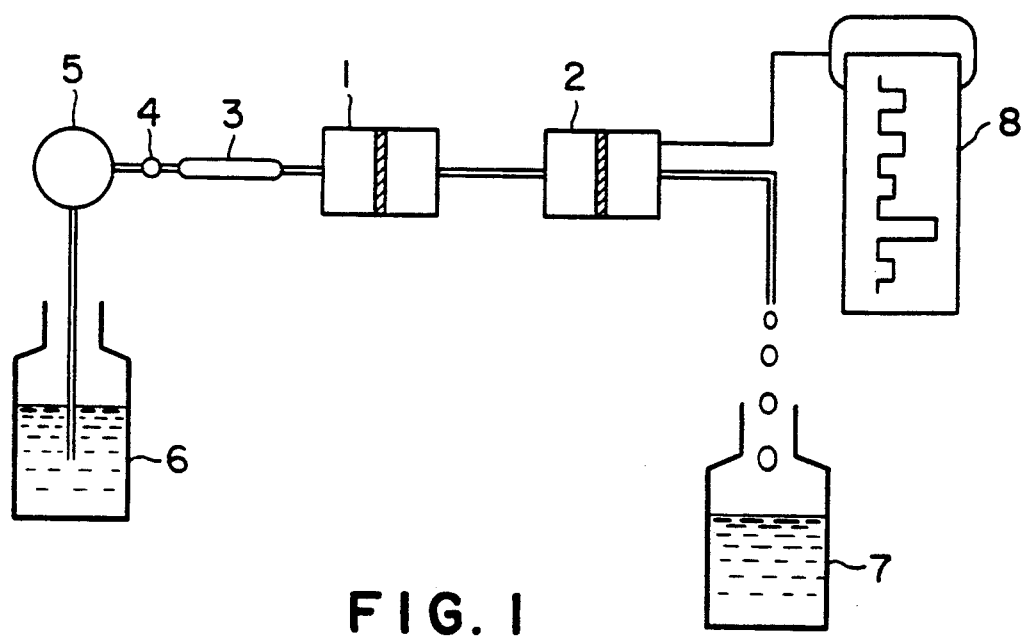
F I G. 1
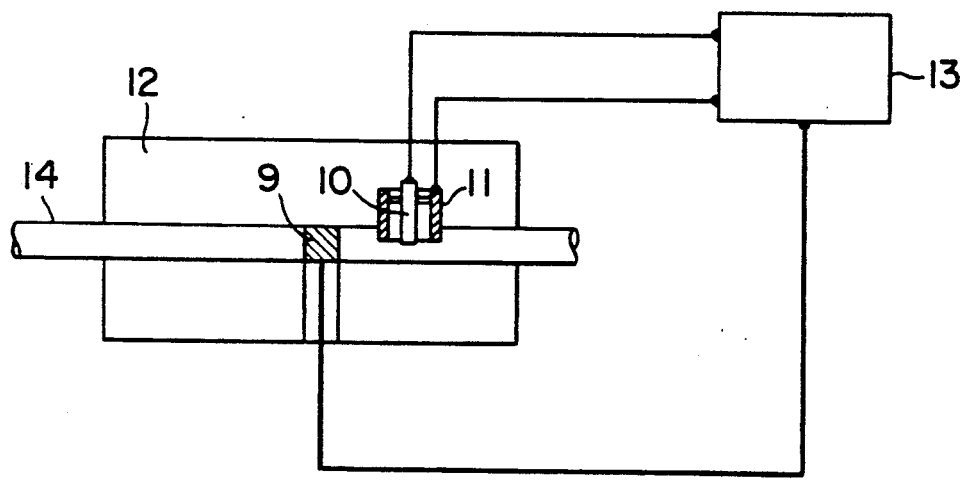
F I G. 2

ELECTRODE FOR ELECTROCHEMICAL DETECTORS

BACKGROUND OF THE INVENTION

1. Field of the Invention

This invention relates to an electrode for a coulometric type of electrochemical detector capable of providing a highly sensitive detection of trace amounts of electrically active substances isolated by, for example, liquid chromatography, a process for preparing it and an analytical apparatus in which it is built.

2. Background Art

Heretofore, electrochemical detectors having electrodes designed therefor have been used for the detection and determination of trace amounts of electrochemically active substances contained in biopsy such as catecholamines and their metabolites because they can be used in combination with liquid chromatography to enable the highly sensitive detection of such substances.

Amperometric types of electrodes have so far been used as such electrodes for electrochemical detectors, but it has been found that they cannot be applied to more precise analysis because of their limited resolving power. Known as the electrode capable of enabling detection to the highest sensitivity is one used with a coulometric type of electrochemical detector.

Essentially required for such an electrode for the coulometric type of electrochemical detector is that:

(1) it should be formed of an electrically conductive material having a high surface area sufficient for efficient reactions, because it is desired that the substances to be detected pass through an electrode cell while they are all electrochemically converted;

(2) its surface should have a low polarity and be chemically stable since it is required to possess durability over an extended period of time; and (3) it should have a uniform pore diameter distribution so as to prevent clogging in electrode cells.

As electrically conductive materials which can meet such conditions (1), (2) and (3), it is preferred to use carbonaceous substances, inter alia, those in the form of graphite that is of low polarity and chemically stable, as known from U.S. Pat. No. 4804455.

However, such graphite-form carbonaceous substances as set forth in U.S. Pat. No. 4804455 are so small in their surface area and so poor in their mechanical stability that they place some limitation upon being used as materials for electrodes for the coulometric type of electrochemical detectors in particular.

SUMMARY OF THE INVENTION

As a result of intensive studies made with the above problem in mind, the present inventors have now found that a formed product of a porous, graphitic carbon having specific physical properties can be advantageously used as electrodes for electrochemical detectors, esp., the coulometric type of electrochemical detectors, since it is of no surface polarity, shows stable chemical properties, has a properly large surface area and possesses a uniform pore diameter so that clogging, etc. cannot occur over an extended period of time, and have therefore accomplished the present invention.

Thus, the electrode for electrochemical detectors according to the present invention comprises a formed product of a porous, graphitic carbon having the following physical properties (1), (2) and (3):

(1) an average pore size of 0.1 to 50 $\mu$m;

(2) a specific surface area of 10 $m^2/g$ or more; and (3) an average interlaminar spacing ($d_{002}$) of carbon of 3.35 to 3.42 Å as determined by X-ray diffraction analysis.

The present inventors have also found that such an electrode may preferably be used in a multi-stage detector system for liquid chromatography.

Thus, the present invention further provides an analytical apparatus comprising an analytical column for liquid chromatography and at least one coulometric type of electrochemical detector, said electrochemical detector having an electrode comprising a formed product of a porous, graphitic carbon having the following physical properties (1), (2) and (3):

(1) an average pore size of 0.1 to 50 $\mu$m;

(2) a specific surface area of 10 $m^2/g$ or more; and (3) an average interlaminar spacing ($d_{002}$) of carbon of 3.35 to 3.42 Å, as determined by X-ray diffraction analysis.

Because there is chemical stability and a lack of polarity and because it has a properly large specific surface area, improved electrochemical conversion properties and a pore diameter of proper and uniform size, the electrode for electrochemical detectors according to the present invention is substantially unlikely to be clogged even upon use as an electrode of an electrochemical detector over an extended period. A drop in its performance due to deterioration is also substantially unlikely to occur. Thus, when that electrode is used as the electrode of a coulometric type of electrochemical detector in a liquid chromatography apparatus, its improved electrochemical conversion properties can be maintained over an extended period so that trace amounts of substances isolated by liquid chromatography can be detected at high sensitivity and over an extended period.

If a multi-stage arrangement of detectors, each having this electrode, is used in combination with liquid chromatography, then it is possible to enable the selective and highly sensitive detection of many types of trace amounts of substances by a single analytical operation. Thus, it is possible to enable the easy detection of biosubstances which have so sophisticated compositions that difficulty is involved in their analysis.

BRIEF DESCRIPTION OF THE DRAWINGS

FIG. 1 is a schematic view of one embodiment of the analytical apparatus according to the present invention;

FIG. 2 is a schematic view of one embodiment of the coulometric type of electrochemical detector;

In FIGS. 3 and 4, reference numerals denote peaks of the following substances: 15 ... norepinephrine, 16 ... epinephrine, 17 ... dihydroxy benzoate (internal standard substance), 18 dopamine, 19 vanillylmandelic acid, 20 ... homovanilic acid, 21 ... 5-hydroxyindole-3acetic acid.

DETAILED DESCRIPTION OF THE INVENTION

I. Electrode For Electrochemical Detector

Physical Properties

Figure 3:
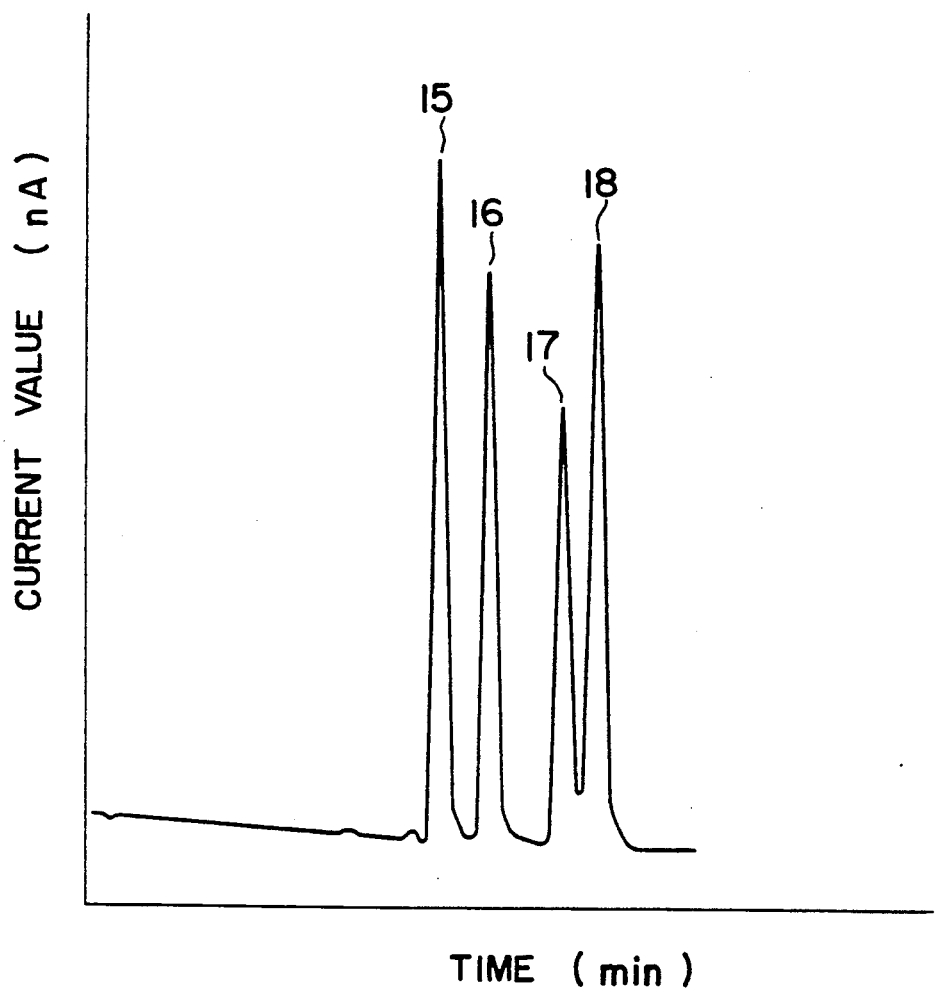
FIG. 3 is an analytical chart showing the results obtained in Example 1.

The electrode for an electrochemical detector and according to the present invention comprises a formed product of a porous, graphitic carbon material having such physical properties as expressed in terms of an average surface pore diameter of 0.1 to 50 μm, preferably 1 to 30 μm; a specific surface area of 10 m$^2$/g or more, preferably 50 m$^2$/g or more; and an average interlaminar spacing ($d_{002}$) of carbon of 3.35 to 3.42 Å, preferably 3.35 to 3.40 Å, as determined by X-ray diffraction analysis.

If the formed product has too small an average pore diameter, then it cannot be used as an electrode over an extended period due to clogging by substances to be detected or impurities. Too large an average pore diameter makes the contact of liquid with the intraelectrode surface so insufficient that efficient analysis cannot be carried out.

Too small a specific surface area renders the electrochemical conversion properties so insufficient that no efficient analysis can be performed. A carbon material having an average interlaminar spacing of carbon of higher than 3.42 Å is less than satisfactory since graphitization is poor and is thus so chemically active on its surface that it can react with substances to be detected to deteriorate its surface and so cannot stand to use over an extended period.

The above average pore diameter may be determined by mercury filling under pressure, whereas the average interlaminar spacing ($d_{002}$) of carbon may be determined by X-ray diffraction and Bragg's equation.

II. Preparation

The electrode of a porous, graphitic carbon according to the present invention may be prepared, for example, by the following methods.

According to one typical preparation method, a composition obtained by mixing together carbon fibers having a specific surface area of 10 m$^2$/g or more, obtained by vapor-phase thermal decomposition of a carbon source compound, a medium containing a carbonizable binder material for binding the carbon fibers and a pore-forming promotor is compacted into a desired shape as by press molding, for example, and the obtained compact is then sintered in a non-oxidizing atmosphere to give the end product.

Carbon Fibers Obtained by Vapor-Phase Thermal Decomposition

The "carbon fibers" used in the above methods and obtained by vapor-phase thermal decomposition refer to fibrous, graphitic carbon materials obtained by thermally decomposing a carbon source compound such as a hydrocarbon or carbon monoxide in the presence of an ultrafine catalyst of a transition metal such as Fe or Co to produce carbon and growing it in a vapor phase. The resulting carbon may further be heated. Since carbon fibers other than the carbon fibers obtained by such vapor-phase decomposition are somewhat poor in crystallizability, it is preferred to use the carbon fibers obtained by the vapor-phase decomposition.

The carbon fibers obtained by the above mentioned vapor-phase decomposition have a specific surface area of 10 m$^2$/g or more, preferably 50 m$^2$/g, as determined by the BET method. The upper limit value is not specifically limited, but should preferably be about 400 m$^2$/g.

A typical method usable for preparing such carbon fibers having a preferably high specific surface area (of 50 m$^2$/g or more) by vapor-phase decomposition is described in, for example, Japanese Patent Application No 63(1988)-322431.

More specifically, the carbon fibers may be prepared by feeding a carbon source compound with a carrier gas into a heating zone in a reactor tube and decomposing the carbon source compound in a vapor-phase space in the presence of an ultrafine catalyst of a transition metal, which catalyst is prepared by the vapor-phase, thermal decomposition of a carbonyl compound of a transition metal in the presence of at least one organic compound containing oxygen and/or sulfur, thereby obtaining graphite whiskers.

The carbon fibers obtained by such vapor-phase decomposition generally have a diameter of 5 μm or less, preferably 0.1 to 2 μm and a length of 1 mm or less, 1 to 500 μm.

Carbonizable Binder Material

The above described carbonizable binder material is used to bind together the carbon fibers obtained by the vapor-phase decomposition at the time of mixing and granulation. As such carbonizable binder materials, use may be made of, e.g., thermosetting resins such as phenolic resin (such as resol resin and novolak resin), furan resin, acrylic resin, epoxy resin and unsaturated polyester resin and thermoplastic resins such as ABS resin, polycarbonate resin and polypropylene resin. Use may also be made of pitch, tar, etc. Most preferable are phenolic resins having a relatively high yield of carbonization, inter alia, liquid phenolic resin or pitch.

Diluent Medium

Diluent media used for making the carbonizable binder material a solution or dispersion may include, for instance, water, methanol, tetrahydrofuran, pyridine, quinoline, benzene and toluene.

The concentration of the carbonizable binder material in the diluent medium may vary depending upon the type of the carbonizable binder material, the type of the diluent medium which is either a solvent or dispersant, the surface area and length of the carbon fibers obtained by the vapor-phase decomposition and mixed with the diluent medium, the porosity and mechanical properties of the resulting porous grains and other factors. Usually, however, that concentration is in a range of 5 to 60% by weight, preferably 10 to 30% by weight.

Pore-Forming Promotor

As the pore-forming promotor used with a view to imparting pores of a sharp pore-size distribution to the formed product of a porous, graphitic carbon material, use may be made of substances which are decomposed and gasified by sintering in a non-oxidizing atmosphere, leaving no or little carbon residue behind. For instance, starch, cellulose, polyethylene oxide, polyvinyl alcohol, etc. may be used to this end. For the addition of this pore-forming promotor, it may be fed into a solution or dispersion of the carbonizable binder material in the diluent medium.

The pore-forming promotor is added to the solution or dispersion of the carbonizable binder material in such an amount that the resulting porous graphitic product has an average pore diameter in a range of 0.1 to 50 μm.

Sintering

The composition obtained as mentioned above is dried and then pressed into a desired shape by a mold press and then heated. By this heating, the carbonizable binder material is carbonized and graphitized, while the poreforming promotor is decomposed, thereby forming porous graphite having pores of a sharp pore-size distribution. Heating is carried out in a non-oxidizing inert gas such as nitrogen or argon gas and at a temperature of 800 to 3,000° C., preferably 1,000° to 2,500° C. Usually, the heating time ranges from 5 to 20 hours.

Porous, Graphitic Carbon

The porous, graphitic carbon product obtained as mentioned above is formed on its surface with a number of pores having an average pore diameter of 0.1 to 50 $\mu$m, preferably 1 to 30 $\mu$m, and has a specific surface area of 10 m$^2$/g or more, preferably 50 m$^2$/g or more. As determined by X-ray analysis, this product shows an average interlaminar spacing ($d_{002}$) of carbon of 3.35 to 3.42 Å, which means that it is graphitic.

This porous, graphitic carbon product is formed into a desired shape as an electrode by cutting for example, and is then built into a coulometric type of electrochemical detector.

III. Use of the Electrode as Working Electrode

The thus produced electrode of the present invention may be used as a working electrode of the coulometric type of detector.

As illustrated in FIG. 2 by way of Example, the electrode of the present invention may be used as a working electrode 9 located in a sample flow path 14.

The apparatus shown in FIG. 2 includes, in addition to the working electrode 9, a reference electrode 10 and a counter electrode 11, an electrolytic cell 12 housing these electrodes, and a coulometer 13 with a built-in potentiostat for impressing a constant potential between the working and counter electrodes on the basis of the reference electrode. As the reference electrode, use may then be made of an ordinary electrode, but most preferable is a silver/silver chloride electrode or an iron ferricyanide/iron ferrocyanide electrode. As the counter electrode, use may also be made of an ordinary electrode. Preferred are electrodes made of corrosion-resistant metals, particularly, platinum, gold or stainless steel.

IV. Analytical Apparatus

As illustrated in FIG. 2 by way of example, the coulometric type of electrochemical detector, in which the electrode of the present invention is incorporated, is suitably used in combination with liquid chromatography, esp., high speed liquid chromatography (HPLC) for the detection and determination of trace amounts of biosubstances.

As liquid chromatography, normal measuring systems may be employed. For example, there is shown in FIG. 1 a double-channeled multi-stage type of detector system in which two electrochemical detectors 1 and 2 of the coulometric type, each with the electrode of the present invention built in, are connected in series to each other.

The system of FIG. 1 includes, in addition to the detectors 1 and 2, an analytical column 3 for liquid chromatography, a sample input port 4, a pump 5, a carrier liquid reservoir 6, a waste liquid reservoir 7 and a recorder 8.

The analytical column and carrier liquid may be arbitrarily selected depending upon the components of samples to be analyzed.

The electrode of the present invention is suitable for the analysis of trace components in biosubstances such as catecholamines or their metabolites. Furthermore, the electrodes are used in a multi-stage type of detector system in which a multiplicity (2 to 30) of detectors are connected in series with one another, a plurality of components in a mixture of complicated trace components, like biosubstances, can be analyzed by a single analytical operation by applying suitably high potentials successively to the respective electrodes.

EXPERIMENTAL EXAMPLES

Example 1

Preparation of Graphitic Carbon Product 3 g of commercially available phenolic resin having a solid content of 65% by weight was added and dissolved in 3 liters of water by heating. This solution was then mixed with 100 g of carbon fibers having a specific surface area of 130 m$^2$/g, an average diameter of 0.2 $\mu$m and an average length of 2 $\mu$m, obtained by the vapor-phase decomposition, 10 g of potato starch and 0.2 g of sodium alginate. The mixed solution was added dropwise in small portions to a 10% aqueous solution of calcium chloride to form a gelatinized liquid in the form of spherical droplets.

The thus obtained spherical droplets were filtered and then dried at room temperature.

Next, the spherical particles were placed in a stainless steel mold 45 mm in diameter, in which they were pressed at a pressure of 0.5 kg/cm$^2$. Afterwards, the obtained compact was cured by heating for 2 hours at a temperature of 200° C. to obtain a cured product. This product was heated to a temperature of 1,000° C. at a heating rate of 70° C./hour, at which temperature it was held for a further 6 hours. Thereafter, it was again heated to a temperature of 2,000° C., at which temperature it was held for a further 15 minutes, and then it was cooled down.

The product thus obtained had a specific surface area of 51 m$^2$/g, an average pore diameter of 3 $\mu$m with a sharp pore-size distribution. As determined by X-ray diffraction, it had an average interlaminar spacing ($d_{002}$) of 3.38 Å, thus indicating a graphitic structure.

Electrochemical Detector

The product of a graphitic structure obtained above was cut into a 5 mm$\times$3 mm electrode for an electrochemical detector, which was then built in an electrochemical detector, as shown in FIG. 2, with Ag/AgCl as a reference electrode and platinum as a counter electrode. This detector was used in combination with high speed liquid chromatography for the analysis of catecholamines as indicated below.

In an isolation column filled with octadecylated silica gel through which a mixed liquid of phosphate buffer (pH: 3.3)/methanol/sodium n-octyl sulfate/EDTA was flowing as a mobile phase, an aqueous solution having norepinephrine, epinephrine, dihydroxy benzoate (internal standard substance) and dopamine dissolved therein was injected, and the eluent was passed through the above electrochemical detector.

As a result, since the rate of electrochemical oxidation was very high (on the order of 99% or more) in the electrochemical cell including the electrode of the present invention, such a chromatogram as shown in FIG. 3 could be obtained even with a trace amount, as small as 20 picograms of the sample.

The lower limit of detection of catecholamines and their metabolites by this detector was 1 picogram or, in terms of sensitivity, this detector was 500 to 1,000 times as high as conventional electrochemical detectors.

Example 2

Using two detectors, each obtained in Ex. 1, a double-channeled multi-stage type of detector system as shown in FIG. 1 was made.

With this system, vanillylmandelic acid, homovanilic acid and 5-hydroxyindole-3-acetic acid in urine, which are the metabolites of catecholamines and serotonin, were analyzed as follows.

In an isolation column filled with octadecylated silica gel through which a mixed liquid of phosphate buffer (pH: 3.1)/acetonitrile (7:1, v/v) was flowing as a carrier liquid, 0.5 μl of urine was injected, and the eluent was passed through the detectors 1 and 2. In the above operation, 620 mV and 720 mV were applied on the electrodes of the detectors 1 and 2, respectively.

Figure 4:
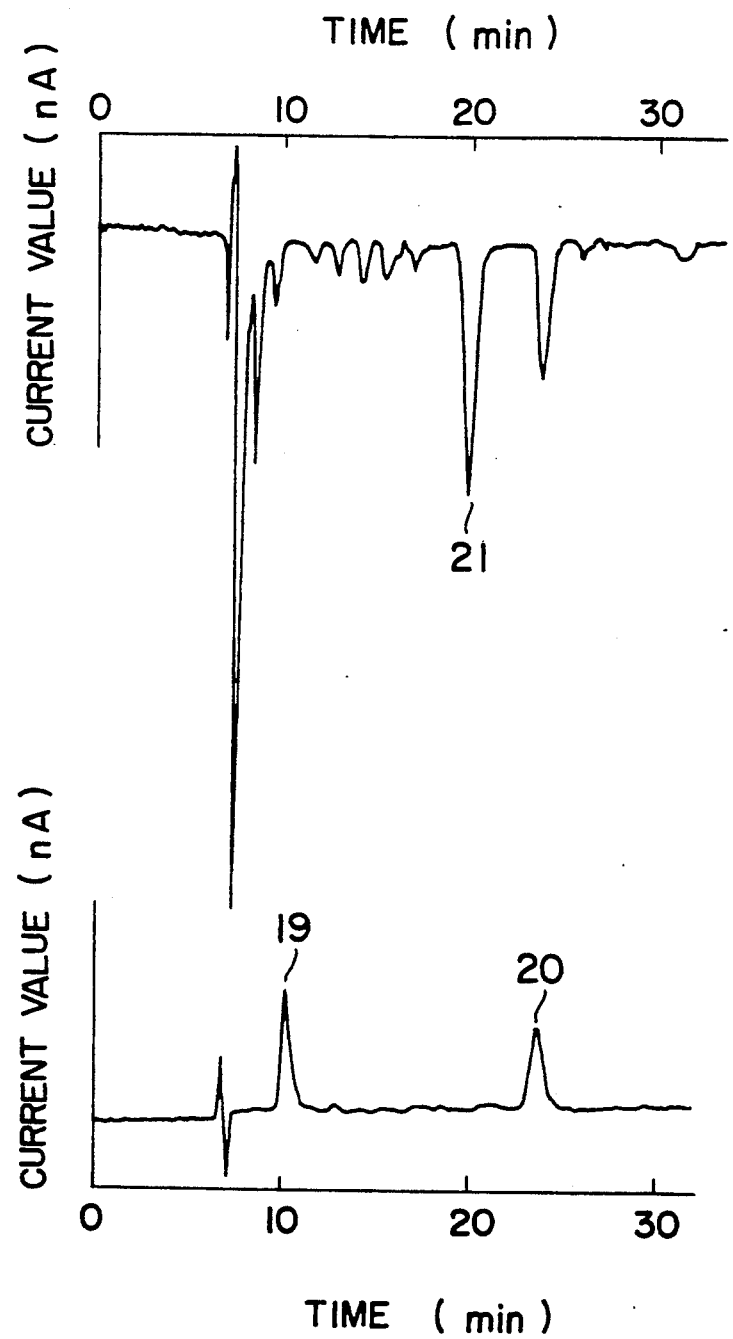
FIG. 4 is an analytical chart showing the results obtained in Example 2.

As a result, since the rate of electrochemical oxidation was very high (on the order of 99% or more) in the coulometric type of detector system including the working electrodes according to the present invention, such a selective and highly sensitive chromatogram as shown in FIG. 4 could be obtained even with the direct injection of urine.

The lower limit of detection of catecholamines, serotonin and their metabolites by this system was 1 picogram or, in terms of sensitivity, this system was 500 to 1,000 times as high as conventional amperometric type of electrochemical detectors.

What is claimed is:

1. A process for producing an electrode for a coulometric type of electrochemical detector, which comprises molding a composition comprising carbon fibers having a specific surface area of 10 m$^2$/g or more, a diameter of 0.01 to 2 μm and a length of 1 to 500 μm obtained by thermally decomposing a carbon source compound in the presence of a catalyst consisting of ultrafine particles of a transition metal to grow carbon in a vapor phase, a medium containing a carbonizable binder material and a pore-forming promotor and, then, sintering the thus molded product in a non-oxidizing atmosphere, said electrode comprising a formed product of a porous, graphitic carbon having the following physical properties (1), (2) and (3):
   (1) an average pore diameter of 0.1 to 50 μm,
   (2) a specific surface area of 50 m$^2$/g or more, and
   (3) an average interlaminar spacing ($d_{002}$) of carbon of 3.35 to 3.42 Å, as determined by X-ray diffraction analysis.

2. A process as claimed in claim 1, wherein said carbon fibers have a specific surface area of 50 m$^2$/g or more.

3. A process as claimed in claim 1, wherein said carbonizable binder material is at least one selected from the group consisting of a thermosetting resin, a thermoplastic resin, pitch and tar.

4. A process as claimed in claim 3, wherein said thermosetting resin is a phenolic resin.

5. A process as claimed in claim 1, wherein said pore-forming promotor is at least one selected from the group consisting of starch, cellulose, polyethylene oxide and polyvinyl alcohol.

6. An analytical apparatus comprising an analytical column for liquid chromatography and at least one coulometric type of electrochemical detector,
   said detector having an electrode comprising a formed product of a porous, graphitic carbon material having the following physical properties (1), (2) and (3):
   (1) an average pore diameter of 0.1 to 50 μm,
   (2) a specific surface area of 50 m$^2$/g or more, and
   (3) an average interlaminar spacing ($d_{002}$) of carbon of 3.35 to 3.42 Å, as determined by X-ray diffraction analysis.

7. An analytical apparatus as claimed in claim 6, wherein said average pore diameter of said electrode is 1 to 30 μm.

8. An analytical apparatus as claimed in claim 6, wherein said average interlaminar spacing ($d_{002}$) of carbon of said electrode is 3.35 to 3.40 Å.

9. A process as claimed in claim 1, wherein said average interlaminar spacing ($d_{002}$) of carbon is 3.35 to 3.40 Å.

* * * * *